United States Patent
Lloyd et al.

(10) Patent No.: US 10,307,295 B2
(45) Date of Patent: Jun. 4, 2019

(54) PROTECTIVE EYEWEAR

(71) Applicant: John George Lloyd, Monte Carlo (MC)

(72) Inventors: John George Lloyd, Monte Carlo (MC); Piers Christian Storey, Church Brow (GB)

(73) Assignee: SCP George TFE, Monte Carlo (MC)

( * ) Notice: Subject to any disclaimer, the term of this patent is extended or adjusted under 35 U.S.C. 154(b) by 449 days.

(21) Appl. No.: 15/014,204

(22) Filed: Feb. 3, 2016

(65) Prior Publication Data

US 2017/0020734 A1    Jan. 26, 2017

(30) Foreign Application Priority Data

Feb. 3, 2015    (GB) .................................. 1501782.5

(51) Int. Cl.
| | | |
|---|---|---|
| *A61F 9/02* | (2006.01) | |
| *A41D 13/11* | (2006.01) | |
| *A41D 27/02* | (2006.01) | |
| *A41D 31/00* | (2019.01) | |
| *A42B 3/18* | (2006.01) | |

(52) U.S. Cl.
CPC .......... *A61F 9/027* (2013.01); *A41D 13/1184* (2013.01); *A41D 27/02* (2013.01); *A41D 31/005* (2013.01); *A42B 3/18* (2013.01); *A61F 9/026* (2013.01)

(58) Field of Classification Search
CPC .................................. A61F 9/027; A42B 3/20
USPC ............................................................. 2/909
See application file for complete search history.

(56) References Cited

U.S. PATENT DOCUMENTS

| | | | | |
|---|---|---|---|---|
| 3,829,900 A | * | 8/1974 | Marangoni | A42B 3/065 |
| | | | | 2/414 |
| 3,877,076 A | | 4/1975 | Summers | |
| 3,952,331 A | | 4/1976 | Melville | |
| 4,133,604 A | * | 1/1979 | Fuller | G02C 3/003 |
| | | | | 351/123 |
| 4,484,364 A | * | 11/1984 | Mitchell | A42B 3/124 |
| | | | | 2/413 |
| 4,657,364 A | * | 4/1987 | Murrell | G02C 3/003 |
| | | | | 351/123 |
| 5,151,778 A | * | 9/1992 | Conley | A45C 11/04 |
| | | | | 2/452 |
| 6,343,860 B1 | | 2/2002 | Pierotti | |
| 6,691,324 B1 | | 2/2004 | Nakamura | |
| 2004/0156011 A1 | * | 8/2004 | David | A61F 9/027 |
| | | | | 351/43 |
| 2004/0261157 A1 | | 12/2004 | Talluri | |
| 2007/0250994 A1 | * | 11/2007 | McNeal | A42B 3/185 |
| | | | | 2/426 |

(Continued)

FOREIGN PATENT DOCUMENTS

| | | |
|---|---|---|
| DE | 3005133 A1 | 8/1981 |
| JP | 2000045118 A | 2/2000 |
| WO | 2005060778 A2 | 7/2005 |

*Primary Examiner* — Tajash D Patel
(74) *Attorney, Agent, or Firm* — James Creighton Wray; Meera P. Narasimhan

(57) ABSTRACT

The application discloses a flexible strap for retaining protective eyewear on a wearer's head. The strap includes an energy absorbing material which is configured to deform to absorb kinetic energy on impact and which is held in contact with a first outer layer. A method of manufacture of the strap is also disclosed.

16 Claims, 8 Drawing Sheets

(56) References Cited

U.S. PATENT DOCUMENTS

Figure 1:
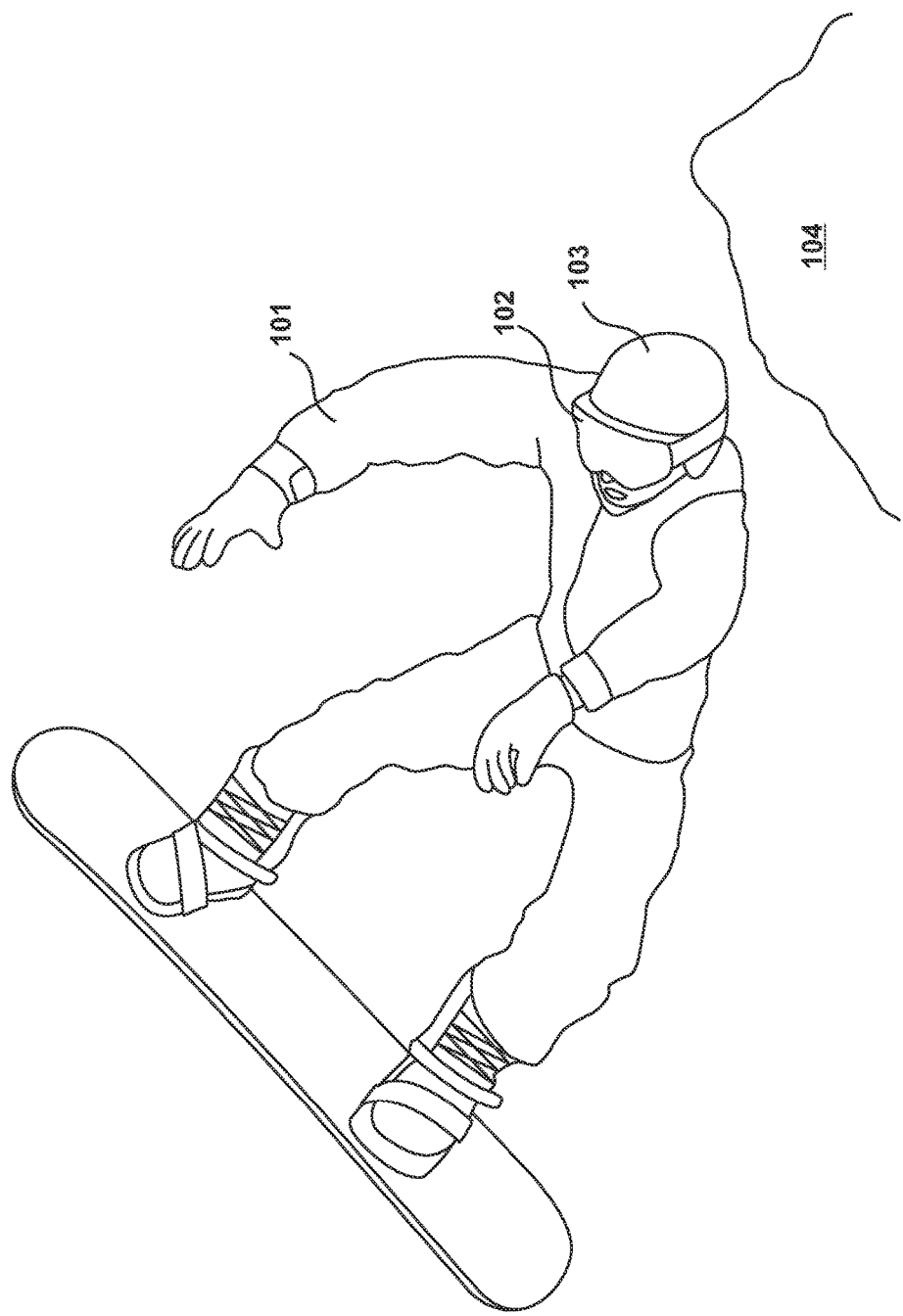

2010/0129573 A1* 5/2010 Kim .................. A41D 31/005
              428/34.1
2013/0019386 A1* 1/2013 Hahn .................. A63B 33/002
              2/431

* cited by examiner

PROTECTIVE EYEWEAR

This application claims the benefit of United Kingdom Application No. GB 15 01 782.5 filed Feb. 3, 2015, which is hereby incorporated by reference in its entirety as if fully set forth herein.

The present invention relates to a flexible strap for retaining protective eyewear on a wearer's head, and a method of manufacturing such a strap. A method of protecting a person's head is also described.

Protective eyewear is often worn by individuals in order to protect the eyes of the individual from debris, chemicals, adverse lighting conditions or other conditions which can cause damage to the eyes or sight of the individual. This type of protective eyewear often takes the form of goggles which include a lens fitted to a frame. The frame is then attached to a strap which allows the frame and lens to be held in position on a wearer's head with the lens covering, and protecting, the eyes.

While protective eyewear focuses on providing protection for the individual's eyes, there is little protection provided to the rest of the individual's head should an impact to the head be received. In this respect, helmets are often worn with protective eyewear.

According to an aspect of the present invention, there is provided a flexible strap for retaining protective eyewear on a wearer's head comprising: an energy absorbing material configured to deform to absorb kinetic energy on impact, said energy absorbing material having a thickness of between 1 and 6 millimeters; and a first outer layer, wherein said energy absorbing material is held in contact with said first outer layer.

In an embodiment, the energy absorbing material comprises a plurality of tubes with each of said tubes being welded to at least one other of said tubes. However, the energy absorbing material may take alternative forms capable of absorbing energy, such as energy absorbing foams and honeycomb structures. Throughout the application, energy absorbing material is taken to include energy absorbing materials incorporating tubes, energy absorbing foams, honeycomb structures and any other suitable energy absorbing materials including viscoelastic foams.

According to a further aspect of the present invention, there is provided a method of manufacturing a flexible strap for retaining protective eyewear on a wearer's head, comprising the steps of obtaining an energy absorbing material having a thickness of between 1 and 6 millimeters, said energy absorbing material being configured to deform to absorb kinetic energy on impact; fabricating a first outer layer of flexible material; and placing said energy absorbing material and said first outer layer together such that they are held in contact with each other.

In an embodiment, the method includes positioning the energy absorbing material between adhesive layers and material layers and applying heat to bond the energy absorbing material to the layers of material.

According to a still further aspect of the present invention, there is provided a method of protecting a portion of a person's head when receiving an impact, comprising the steps of: receiving an impact on a flexible strap for retaining protective eyewear; and absorbing kinetic energy on said impact by means of an energy absorbing material having a thickness of between 1 and 6 millimeters.

Figure 2:
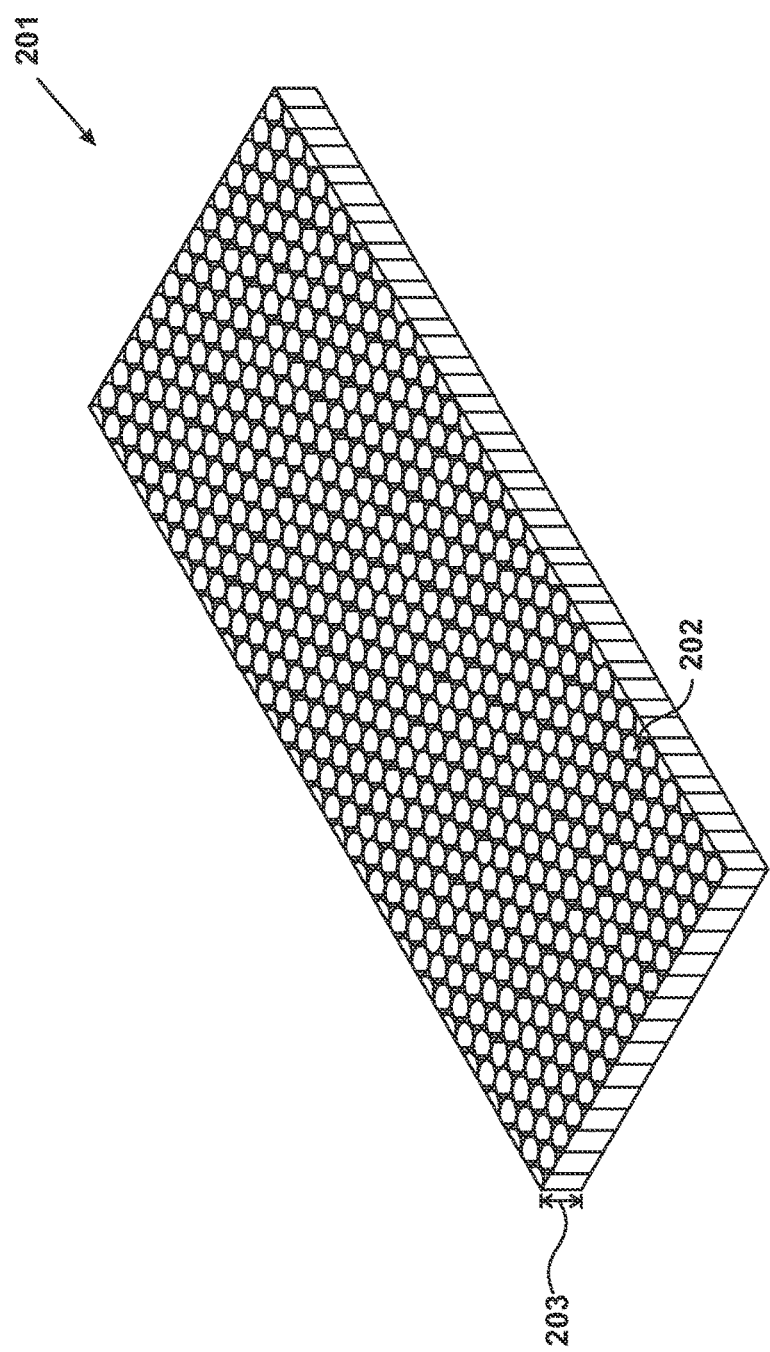
Figure 3:
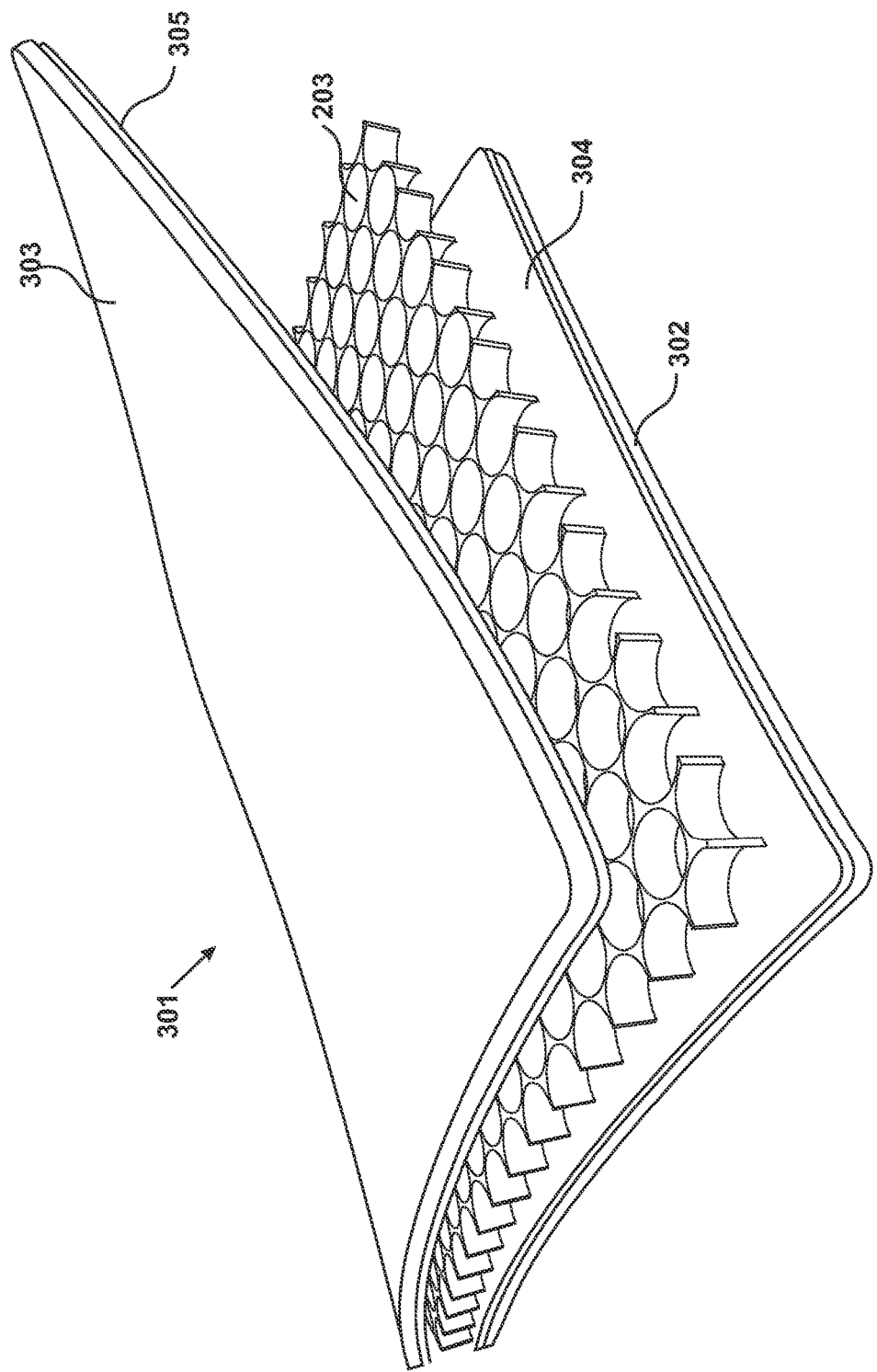
Figure 4:
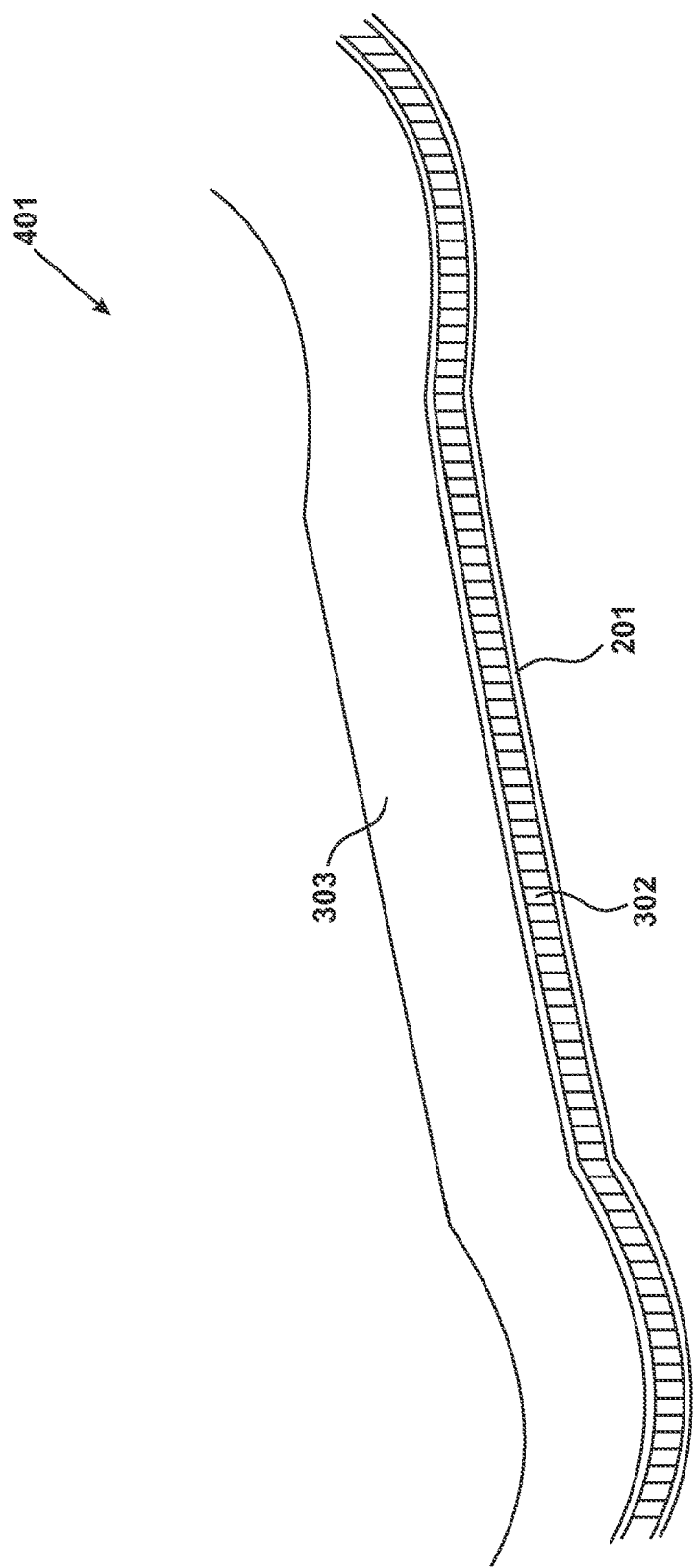
Figure 5:
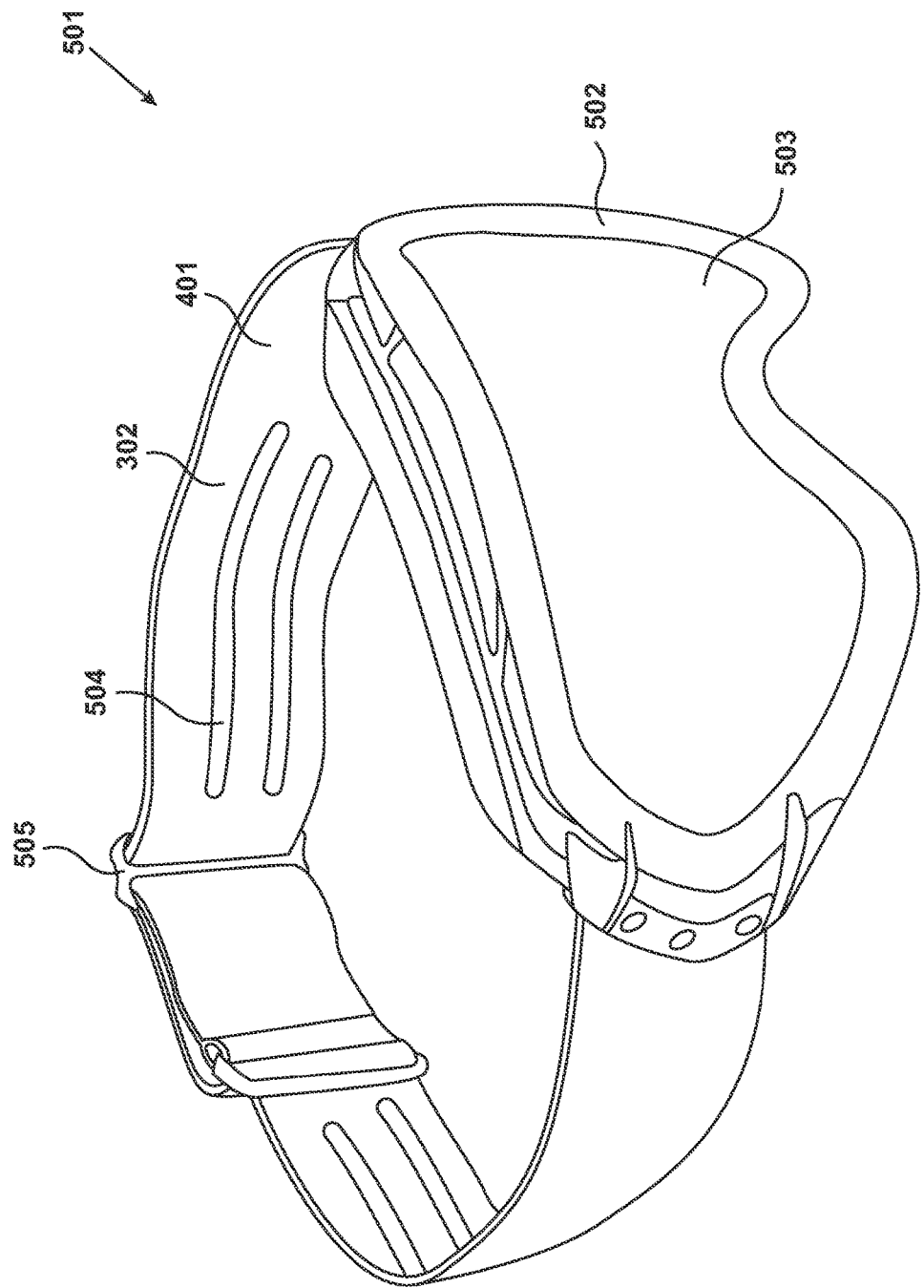
Figure 6:
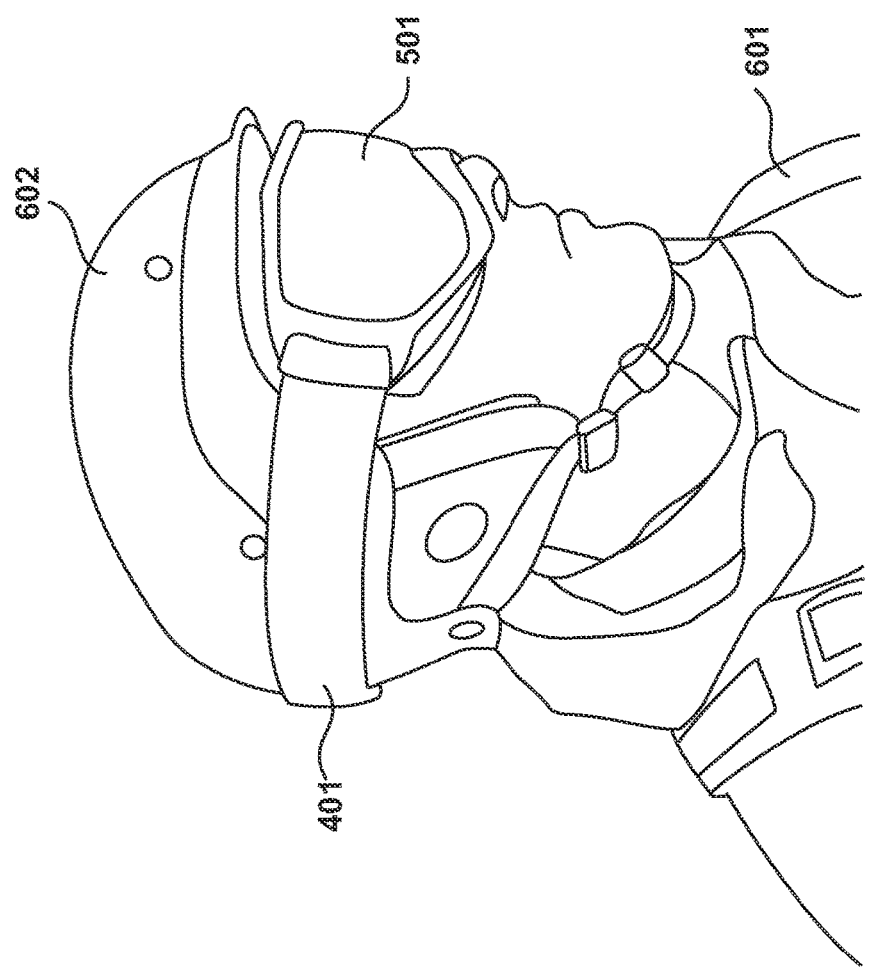
Figure 7:
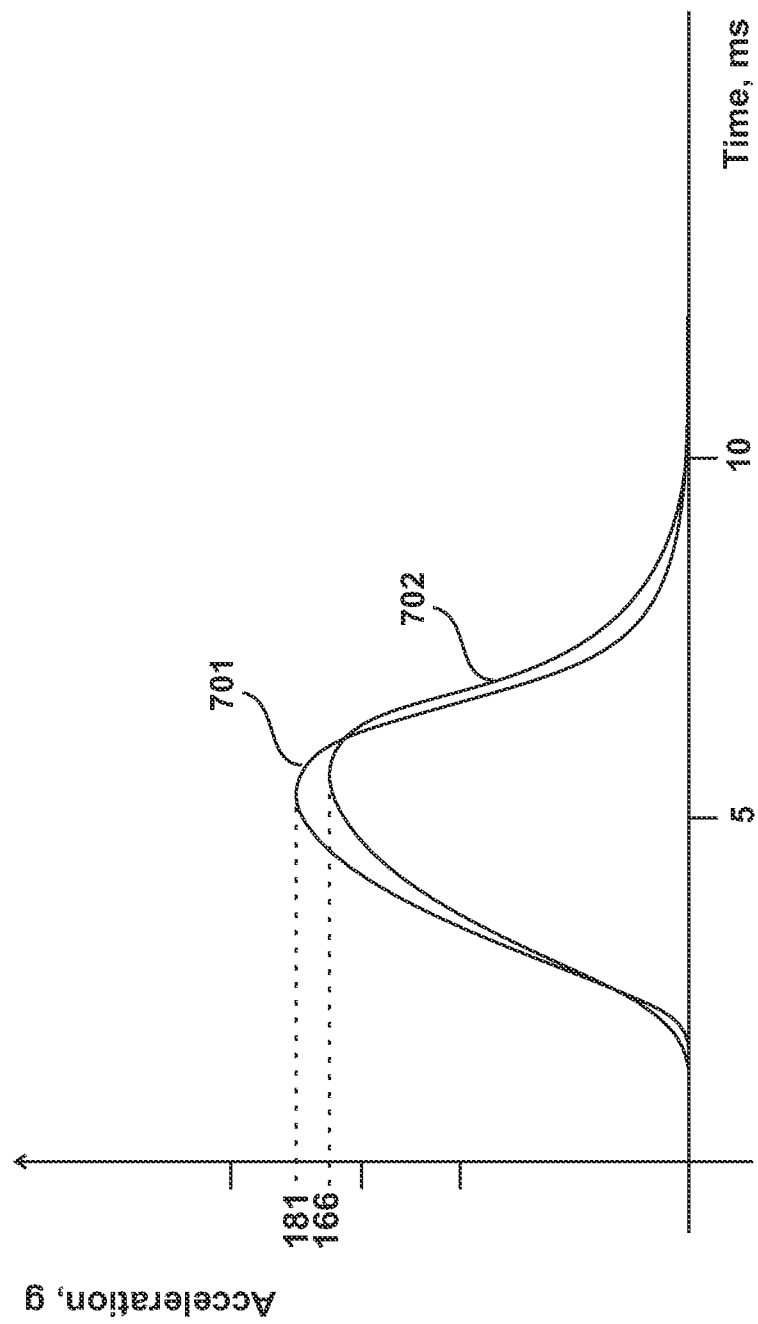
Figure 8:
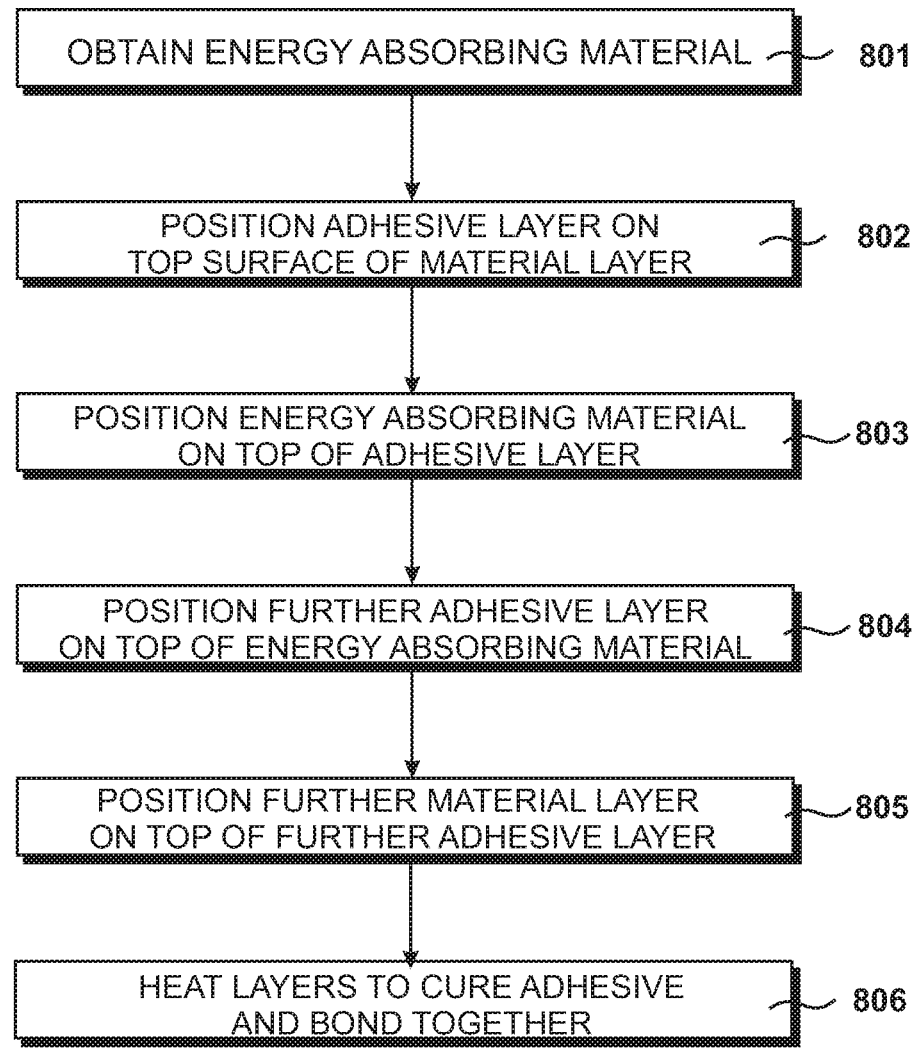

The invention will now be described by way of example only, with reference to the accompanying drawings, of which:

FIG. 1 shows a scenario involving a snowboarder falling over;
FIG. 2 shows a type of energy absorbing material;
FIG. 3 shows an exploded diagrammatic example of the construction of a strap;
FIG. 4 shows a constructed strap;
FIG. 5 shows a flexible strap attached to protective eyewear;
FIG. 6 shows the protective eyewear of FIG. 5 being worn by a person in combination with a protective helmet;
FIG. 7 shows a sample of results of experimental tests conducted on a strap in accordance with the present invention; and
FIG. 8 shows a flowchart illustrating a method of manufacturing protective eyewear.

FIG. 1

A scenario involving an accident experienced by a person 101 is illustrated in FIG. 1. FIG. 1 shows snowboarder 101 having lost their control while taking part in snowboarding activities. In this example, snowboarder 101 wears protective eyewear 102 in the form of ski goggles, as well as a helmet 103 for added protection.

It is known that snowboarders are liable to fall while snowboarding either when losing balance or contact between the snowboard and the snow. In these situations, the snowboarder may be unable to exercise enough control so as to prevent an impact with their head and solid objects, such as rocky outcrop 104. While some protection to this type of impact is offered by helmet 103, protection is not typically provided by eyewear 102. This problem is emphasised when the snowboarder is wearing eyewear without a helmet.

The present invention proposes an alternative to protective eyewear currently known with a view to reducing the amount of energy absorbed by a person in the event of an impact with the head. While the example illustrated refers to snowboarders, it is appreciated that the invention is also applicable in other applications where protective eyewear is worn and in which impacts with the head are also anticipated, for example, in military applications, skiing, motocross, paintballing, cycling or other activities where personal protective equipment is worn.

FIG. 2

The present invention provides a flexible strap for protective eyewear, which strap comprises an energy absorbing material which is configured to deform so as to absorb kinetic energy on impact. An example of the type of energy absorbing material utilised by the present invention is shown in FIG. 2. An example of a material of this type is described in European patent EP 1 694 152 B1 (U.S. Pat. No. 8,082, 599).

Energy absorbing material 201 comprises a plurality of tubes, such as tube 202, each of which are arranged in closely packed arrays so as to minimise the spaces between each of the tubes. Each tube is welded to at least one of the adjacent tubes which improves stability of the connected tubes. This thereby assists in the prevention of global buckling failure modes in the tubes, as each of the tubes acts to support the other adjacent tubes and leads to improved energy absorption properties.

In an embodiment, each tube has a diameter of between one point five millimeter and ten millimeters (1.5 mm-10 mm). In a particular embodiment, the tube diameter is two and a half millimeters (2.5 mm) and has a density of one hundred and ten grams per liter (110 g/l). It is appreciated that, in alternative embodiments, any other suitable tube diameters or densities may be used depending on the required application.

In the embodiment, the width, or thickness 203 of the energy absorbing material 201 is between one millimeter and six millimeters (1 mm and 6 mm). In a specific embodiment, thickness 203 is two millimeters (2 mm). This relatively thin material is advantageous as it allows for flexibility and does not add unnecessary bulk or weight that would need to be carried on a wearer's head. The word flexible is used herein to indicate that a material can be easily bent without breaking; thus the flexible strap easily moulds to the shape of a wearer's head.

In alternative embodiments, the energy absorbing material used in the present invention is any other suitable energy absorbing material, for example, energy absorbing foams such as those made from polyurethane, honeycomb structures (metallic or non-metallic) or viscoelastic foams.

FIG. 3

Energy absorbing material 203 is utilised to form a flexible strap. In the embodiment of FIG. 3, energy absorbing material 203 forms part of a structure 301 comprising a first outer layer of material 302. Structure 301 further comprises a second outer layer of material 303 and, in this embodiment, the first layer and second layer are both fabric layers.

Energy absorbing material 203 is positioned between outer layer 302 and outer layer 303 to effectively form a sandwich structure capable of absorbing energy in impact. Thus, to form a strap of the type as will described in FIGS. 4 and 5, energy absorbing material 203 is attached to fabric layers 302 and 303 and secured in place by means of adhesive layers 304 and 305 such that the energy absorbing material 203 is integrally bonded to each of the outer layers 302 and 303.

Adhesive layers 304 and 305 are adhesive films and are configured to melt under application of heat to bond the outer layers 303 and 304 to the energy absorbing material 203. It is appreciated, however, that any other suitable adhesive can be used to secure the energy absorbing material to the outer layers.

In an alternative embodiment to that shown in FIG. 3, the outer layers 302 and 303 are manufactured from a non-fabric material, such as polymer sheets, for example, polyurethane sheets. In further embodiments, the outer layers are manufactured from polyester, nylon or spandex. It is further appreciated that other suitable materials can be used such as an elasticated material to provide flexibility in the outer layers.

In alternative embodiments, the structure comprises a single outer layer only, to which the energy absorbing material of any type previously described is secured. In one such embodiment, a thin layer of energy absorbing foam is used for the energy absorbing material with a single fabric layer.

FIG. 4

In accordance with the present invention, the structure 301 of FIG. 3 is constructed to form a strap 401, a portion of which is depicted in FIG. 4.

Strap 401 comprises energy absorbing material 201 of any of the types previously described which is configured to deform to absorb kinetic energy on impact. Strap 401 is suitable for retaining protective eyewear on a wearer's head in the manner shown in previous FIG. 1.

As described in FIG. 3 previously, strap 401 comprises a first outer layer 302 and a second outer layer 303 with the energy absorbing material attached to first outer layer 302 and second outer layer 303 by means of an adhesive. In the embodiment, at least one of the outer layers 302, 303 is manufactured from a fabric material.

Thus energy absorbing material 201 is held in contact with at least one outer layer such that, in use, energy absorbing material 201 forms an integral piece of the strap which is not easily removed. In this manner, in the illustrated embodiment, energy absorbing material 201 is sandwiched between two outer layers and acts as a core material which is maintained as part of the strap.

In the embodiment, energy absorbing material 201 is relatively thin and in the region of between one millimeter (1 mm) and six millimeters (6 mm), and thus is flexible enough to enable strap 401 to conform around an object, for example, the head of a wearer of protective eyewear.

In the embodiment described in FIG. 4, the energy absorbing material is shown as a continuous piece which is configured to extend along the whole length of the strap. In alternative embodiments, the energy absorbing material is composed of several pieces of energy absorbing material such that the pieces are placed at intervals along strap 401 with gaps or spaces therebetween. These gaps and portions not only reduce the amount of material used while also increasing flexibility of the strap. Additionally, the gaps may be utilised to and may be used to accommodate, for example, an adjustable mechanism for adjusting the length of the strap.

In a further embodiment, the energy absorbing material is placed in a pocket or a plurality of pockets incorporated as part of the strap, either as a continuous piece or as separate pieces of the energy absorbing material. In this way the energy absorbing material 201 is held in contact with the outer layers. The pocket may be shaped to the exact shape of the energy absorbing material such that the outer layers are taut against the energy absorbing material.

Other embodiments are envisaged where the flexible energy absorbing material is held in contact with at least one outer layer, such that they form an integral strap, in other ways.

FIG. 5

Protective eyewear 501 is shown in FIG. 5 comprising the strap 401, a frame 502 and a lens 503. Protective eyewear 501 is shown as a pair of goggles, of the type suitable for snowboarding or skiing or other activities such as motocross, paintballing, cycling, military or any other activities in which personal protective equipment (PPE) is worn.

Strap 401 includes silicone beading 504 on the surface of outer layer 302 of strap 401 which enables the strap to more effectively grip onto a helmet in the manner which will be described in FIG. 6. Strap 401 also includes an adjustable mechanism 505, in the form of a buckle which enables the length of strap 401 to be adjusted. Additionally, strap 401 comprises an elasticated material to enable the protective eyewear 501 to fit more easily onto a wearer's head. Strap 401 is also configured to be breathable so as to allow a flow of air therethrough. In particular, strap 401 may comprise breathable fabrics or other materials which include air holes which correspond to the holes in the cells of energy absorbing material 201. Thus, comfort and air flow is increased around the wearer's head.

Protective eyewear 501 is attachable to a helmet worn by a wearer by means of strap 401, in the manner which will now be described with respect to FIG. 6.

FIG. 6

Protective eyewear 501 is shown in FIG. 6 being worn by a person 601. Person 601 is also shown wearing a protective helmet 602. Protective eyewear 501 is configured to be attachable to helmet 602, which is typically of the type worn in sports activities in conjunction with protective eyewear.

In combination with the protective eyewear 501, and, in particular the strap 401 of protective eyewear 501, the amount of energy absorbed in impact is increased when the protective eyewear is worn with a helmet compared to a helmet alone. This will be described in further detail in FIG. 7.

Strap 401 is configured to provide increased protection to the wearer 601 when combined with helmet 602. In particular, strap 401 is anticipated as being able to reduce the peak acceleration when impacted to between one hundred and sixty g (160 g) and one hundred and seventy g (170 g) compared to between one hundred and seventy five g (175 g) and one hundred and eighty five g (185 g). This indicates a reduction of around six percent (6%) in peak acceleration; however, it is appreciated that peak acceleration may be reduced by at least twenty five (25%) to thirty percent (30%). In other embodiments therefore, strap 401 is able to withstand a peak acceleration of between eighty g (80 g) and three hundred g (300 g) depending on what is required.

Strap 401 is also configured to function with the helmet and correspond to any contours present in the helmet. In particular, strap 401 is configured to be breathable by comprising a breathable outer material and utilising the cells within the energy absorbing material forming part of the strap 401. In this way, strap 401 does not restrict air vents in helmet 602 and allows air to be vented from the inside of the helmet.

FIG. 7

A graph depicting experimental results of tests on protective eyewear in accordance with the present invention is shown in FIG. 7.

Impact tests in accordance with the requirements for ski helmets under standard EN 1077:2007 were performed using a known open face ski helmet of the type readily available on the market.

In a first test, the helmet alone was dropped at a height of one hundred and fifty eight centimeters (158 cm) at a speed of five point four meters per second (5.4 m/s) and peak acceleration due to gravity (measured in g) was recorded. From this, HIC (Head Injury Criteria) values were calculated. HIC is a known measurement widely used in impact testing to assess the likelihood of serious head injury to a person involved in such an impact. Specifically, it is desirable to achieve as low a value as possible so as to minimise the injury sustained by a person subjected to impact.

The results of the first test are indicated by curve 701. Specifically, a peak acceleration was recorded at around five milliseconds (5 ms) of one hundred and eighty one g (181 g). This entire impact recorded an HIC value of nine hundred and forty six (HIC 946).

In the second test, a strap in accordance with the present invention was attached to a helmet using a two millimeter (2 mm) thick energy absorbing material of the type described in European patent EP 1 694 152 B1 (U.S. Pat. No. 8,082,599). Again, the helmet with strap was dropped at a height of one hundred and fifty eight centimeters (158 cm) at a speed of five point four meters per second (5.4 m/s) and peak acceleration due to gravity (measured in g) was recorded. Similarly, HIC values were calculated from the results.

The results of the second test are indicated by curve 702, which shows a comparative peak acceleration of one hundred and sixty six g (166 g) at around five milliseconds (5 ms) and resulted in a comparative HIC of eight hundred and twelve (HIC 812).

In comparison, these results indicate that using the strap in combination with the helmet results in an eight percent (8%) reduction in the peak acceleration due to gravity (g) and a fourteen percent (14%) reduction in the HIC value. Thus, when using the strap in accordance with the present invention in conjunction with a standard helmet, it can be seen that the chances of a wearer suffering a severe head injury are greatly reduced.

The results shown in FIG. 7 reflect a particular side of the helmet subjected to impact, although similar results were obtained from tests involving the opposite side with a nine percent (9%) reduction in peak acceleration due to gravity (g) and an eleven percent (11%) reduction in the HIC value. However, it is appreciated that the strap in accordance with the present invention is capable of reduction in peak acceleration of at least twenty-five percent (25%) and also reduction in the HIC value by at least twenty-five percent (25%).

FIG. 8

A flowchart illustrating the process of a method of manufacturing a strap of the type previously described is shown in FIG. 8.

At step 801, an energy absorbing material is obtained. The energy absorbing material is any suitable energy absorbing material such as the type of material described in European patent EP 1 694 152 B1 (U.S. Pat. No. 8,082,599). The material is of a thickness that allows flexibility. Manufacture of the energy absorbing material of this kind is obtained by extruding tubes with an inner circumference of a first material and an outer circumference of a second material which has a lower melting point than the first material. The extruded tubes are then cut to a predetermined length before being arranged into the energy absorbing material as shown in FIG. 2. Heat is then applied to the energy absorbing material so as to melt a portion of the outer circumferences without melting the inner circumferences.

In an alternative embodiment, the energy absorbing material obtained is a honeycomb structure, energy absorbing foam or similar which are manufactured by methods known in the art.

At step 802, a first layer of material is obtained and a first adhesive layer is positioned in contact with a top surface of the first layer of material. At step 803, the energy absorbing material is positioned in contact with and on top of the first adhesive layer such that the first adhesive layer is positioned between the first layer and the energy absorbing material. In this way, the strap comprises a single layer of fabric or other suitable material and the energy absorbing material attached thereto. Heat can then be applied in the manner of step 805 so as to bond the material layer to the energy absorbing material.

A further, second adhesive layer is obtained at step 804 and positioned on a top surface of the energy absorbing material such that the energy absorbing material is now sandwiched between the two adhesive layers. A further material layer is obtained at step 805 and positioned on top of the second adhesive layer such that the second adhesive layer is positioned between the energy absorbing material and the second material layer. Thus, in this way, the structure is laid up in a manner substantially similar to that shown in FIG. 3, such that the energy absorbing material is secured between and held in contact with two material layers, such as fabric.

As described previously, in an alternative method of manufacture this second outer layer is not used.

At step 805 heat is applied to the layers which melts the adhesive and cures it such that the first and second adhesive layers bond the energy absorbing material to the first and second material layers respectively to form a strap with the energy absorbing material sandwiched therebetween which is substantially similar to that as shown and described previously in FIG. 4. An adjustable mechanism may then be added to the strap and the strap can then be added to the frame of protective eyewear such as the goggles shown in FIG. 5.

As described previously, an alternative method of manufacture comprises the steps of fabricating a pocket from two outer layers of material and placing the energy absorbing material in the pocket, so that the energy absorbing material is held in contact with the outer layers.

The invention claimed is:

1. A flexible strap for retaining protective eyewear on a wearer's head, comprising:
    an energy absorbing material configured to deform to absorb kinetic energy on impact, said energy absorbing material having a thickness of between 1 and 6 millimeters, and comprising a plurality of tubes, with each of said tubes being welded to at least one other of said tubes; and
    a first outer layer;
    wherein said energy absorbing material is held in contact with said first outer layer.

2. The flexible strap of claim 1, wherein said energy absorbing material comprises energy absorbing foam.

3. The flexible strap of claim 1, wherein said energy absorbing material is held in contact with said first outer layer by an adhesive layer between said energy absorbing material and said first outer layer.

4. The flexible strap of claim 1, further comprising a second outer layer, wherein said energy absorbing material is positioned between said first outer layer and said second outer layer and is held in contact with both layers.

5. The flexible strap of claim 4, wherein said first outer layer and said second outer layer form a pocket, and said energy absorbing material is held in contact with said first and second outer layers by being retained within said pocket.

6. The flexible strap of claim 4, wherein at least one said outer layer is manufactured from one of the following group: a fabric, polyurethane, elastic material, polyester, nylon, spandex.

7. The flexible strap of claim 1, further comprising an adjustable mechanism to allow adjustment of the length of said flexible strap.

8. The flexible strap of claim 1, wherein said flexible strap comprises an elasticated material.

9. The flexible strap of claim 1, wherein said flexible strap is configured to be breathable such that air is free to flow therethrough.

10. Protective eyewear comprising a flexible strap according to claim 1.

11. A helmet comprising the protective eyewear of claim 10, wherein said protective eyewear is configured to provide increased protection to a wearer's head in combination with said helmet.

12. The helmet comprising the protective eyewear according to claim 11 wherein said flexible strap is configured to withstand a peak acceleration of between 80 and 300 g.

13. A method of manufacturing a flexible strap for retaining protective eyewear on a wearer's head, comprising the steps of:
    obtaining an energy absorbing material having a thickness of between 1 and 6 millimeters, said energy absorbing material being configured to deform to absorb kinetic energy on impact, including the steps of;
    extruding tubes with an inner circumference of a first material and an outer circumference of a second material, said second material having a lower melting point than said first material;
    cutting predetermined lengths of said extruded tubes;
    arranging said predetermined lengths into said energy absorbing material; and
    applying heat to melt a portion of said outer circumferences without melting respective inner circumferences;
    fabricating a first outer layer of flexible material; and
    placing said energy absorbing material and said first outer layer together such that they are held in contact with each other.

14. The method of manufacturing a flexible strap of claim 13, wherein said step of placing said energy absorbing material and said first outer layer together comprises the steps of:
    positioning a first adhesive layer in contact with a first surface of said first outer layer;
    positioning said energy absorbing material in contact with said first adhesive layer such that said first adhesive layer is positioned between said first outer layer and said energy absorbing material;
    applying heat to said first outer layer, said first adhesive layer and said energy absorbing material such that said first adhesive layer bonds said energy absorbing material to said first outer layer.

15. The method of manufacturing a flexible strap of claim 14, further comprising the step of:
    positioning a second adhesive layer on a top surface of said energy absorbing material;
    positioning a second outer layer on top of said second adhesive layer such that said second adhesive layer is positioned between said energy absorbing material and said second outer layer; and
    applying heat to said second outer layer, said second adhesive layer and said energy absorbing material such that said second adhesive layer bonds said energy absorbing material to said second outer layer.

16. The method of manufacturing a flexible strap of claim 13, further including the steps of:
    fabricating a second outer layer of flexible material;
    wherein said step of placing said energy absorbing material and said first outer layer together comprises the steps of:
    fabricating a pocket from said first outer layer and said second outer layer; and
    placing said energy absorbing material into said pocket.

* * * * *